(12) United States Patent
Strong et al.

(10) Patent No.: US 7,081,090 B2
(45) Date of Patent: Jul. 25, 2006

(54) PROTECTIVE SHEATH FOR ILLUMINATION ASSEMBLY OF A DISPOSABLE VAGINAL SPECULUM

(75) Inventors: James G. Strong, Skaneateles, NY (US); Dale C. Saddlemire, Cortland, NY (US); Scott G. Spanfelner, Camillus, NY (US); Allan I. Krauter, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 479 days.

(21) Appl. No.: 10/393,848

(22) Filed: Mar. 21, 2003

(65) Prior Publication Data
US 2004/0186355 A1    Sep. 23, 2004

(51) Int. Cl.
*A61B 1/32* (2006.01)
(52) U.S. Cl. .................................................. 600/220
(58) Field of Classification Search .............. 600/203, 600/220, 221, 223, 226, 245
See application file for complete search history.

(56) References Cited

U.S. PATENT DOCUMENTS

| | | | |
|---|---|---|---|
| 3,716,047 A | 2/1973 | Moore et al. | |
| 3,890,961 A | 6/1975 | Moore et al. | |
| 4,143,652 A * | 3/1979 | Meier et al. | 600/203 |
| 4,392,853 A | 7/1983 | Muto | |
| 4,597,383 A * | 7/1986 | VanDerBel | 600/223 |
| 4,766,887 A | 8/1988 | Cecil, Jr. et al. | |
| 4,914,521 A * | 4/1990 | Adair | 348/375 |
| 5,251,613 A * | 10/1993 | Adair | 600/109 |
| 5,562,602 A * | 10/1996 | Yabe et al. | 600/121 |
| 5,785,643 A * | 7/1998 | Lynn | 600/125 |
| 6,379,296 B1 | 4/2002 | Baggett | |
| 6,379,299 B1 | 4/2002 | Borodulin et al. | |
| 2002/0133058 A1 | 9/2002 | Calderwood | |

FOREIGN PATENT DOCUMENTS

| | | |
|---|---|---|
| WO | 96/27322 | 9/1996 |
| WO | 00/41614 | 7/2000 |

OTHER PUBLICATIONS

Centurion Disposable Vaginal Specula; Tri-State Hospital Supply Corporation; from website www.tshsc.com/pages/product.html; Jul. 24, 2001; 2 Pages.

\* cited by examiner

*Primary Examiner*—Eduardo C. Robert
*Assistant Examiner*—David Comstock
(74) *Attorney, Agent, or Firm*—Peter J. Bilinski

(57) ABSTRACT

A protective sheath assembly for a vaginal speculum assembly includes a disposable vaginal speculum and a reusable illumination assembly that is releasably attached to the speculum. The sheath assembly is attachable to the handle of said speculum to cover the illumination assembly while the speculum is in use and permits the illumination assembly to be easily released from the assembly following use.

37 Claims, 8 Drawing Sheets

PROTECTIVE SHEATH FOR ILLUMINATION ASSEMBLY OF A DISPOSABLE VAGINAL SPECULUM

FIELD OF THE INVENTION

The invention relates to the field of medical diagnostic instruments and more particularly to a protective sheath for an illumination assembly of a disposable vaginal speculum.

BACKGROUND OF THE INVENTION

A number of disposable plastic vaginal specula have been developed, such as described, for example, in U.S. Pat. Nos. 3,716,047 and 4,766,887, among others. These disposable vaginal specula are highly useful for high-volume clinical users. The former disposable speculum, for example, is made from a transparent plastic material, such as polystyrene, including a fixed blade portion, a movable blade portion and a slide portion permitting the blades to adjustably assume at least one of a plurality of open positions for conducting a cervical examination.

Illumination systems, such as the Welch Allyn 78010 and 78810 illuminator utilizing the 78000 and 78800 illuminator have been incorporated into the above disposable specula to enhance the examination. A miniature halogen or other incandescent light source is retained in an assemblage that is releasably insertable into a slot provided in a hollow leg of the fixed blade member of the speculum. A curved light conducting bar relays light from the lamp of the illumination assembly along a longitudinal axis of the fixed blade member of the speculum to a medical target area.

One ever present problem that has been faced since the introduction of illumination assemblies as described above is that of contamination due to exigencies of the examination process itself and the normal tendency for body fluids, etc., to make their way to the illumination assembly. While the above described specula are disposable, the illumination assemblies are intended for reuse and therefore excess contamination is a problem that reduces efficiency for the physician and/or gynecologist, given that the illumination assembly therefore requires cleaning prior to each patient use.

SUMMARY OF THE INVENTION

It is therefore a primary object of the present invention to overcome the above-noted deficiencies of the prior art.

It is another primary object of the present invention to better protect the illumination assembly of a disposable vaginal speculum system during examination.

It is yet another object of the present invention to provide a relatively inexpensive covering for an illuminator assembly used with a disposable vaginal speculum that reduces excess contamination and provides for easier cleaning of the illuminator.

Therefore and according to a preferred aspect of the present invention, there is provided a vaginal speculum assembly comprising:

a disposable speculum having a handle;

an illumination assembly including a light source retained within a housing that is releasably attached to said speculum, said illumination assembly further including a cord extending from said housing;

a protective sheath;

a support member attachable to the handle of said speculum onto which said protective sheath is mounted in a stored condition;

wherein said sheath is deployable, releasing said sheath from its stored condition so as to cover said illumination assembly including a portion of said extending portion during an examination process.

Preferably, the support member includes retaining means for retaining the sheath in the stored condition until the user has mounted the illumination assembly to the disposable speculum prior to the examination process.

According to one embodiment, the retaining means includes an elastic member which compresses and retains the stored sheath, the elastic member being held by supporting features appropriately located on the support member.

The support member retains the protective sheath as a compressed cylinder overlaying a spool-like portion of the member in the stored condition. The support member is hollow and includes openings through which a portion of the illumination assembly passes. This arrangement permits the sheath, when deployed, to cover the illumination assembly as a sleeve, and further permits the release of said illumination assembly in order to discard the disposable speculum and the attached sheath assembly when the examination process is completed.

In addition, the sheath preferably includes a tail portion that assists in the deployment of the sheath from its stored position and wherein the sheath can be shaped to conform to aspects of the illumination assembly. For example, the sheath can be properly sized to cover the extending cord and lamp enclosure as well as an inline switch assembly.

According to another preferred aspect of the invention, there is disclosed a method for protecting an illumination assembly of a disposable vaginal speculum from contamination during use thereof, said method comprising the steps of:

attaching a protective sheath assembly to said disposable speculum prior to use thereof, said sheath assembly including a support member that is mounted to said speculum and includes a protective sheath disposed on said support member in a stored condition;

attaching the illumination assembly to said disposable speculum;

deploying said protective sheath from said stored condition prior to use of said speculum so as to cover said illumination assembly.

Preferably, the method further includes the step of placing the speculum and attached illumination assembly over a refuse container and while still holding the extending cord of the illumination assembly, easily discarding the remainder of the assembly.

An advantage of the herein described invention is that the illumination assembly is better protected during the examination process, thereby improving the efficiency of patient flow in the office without having to create additional inventory.

It is another advantage in that the sheath preferably includes an extending tail portion that assists in the deployment of the sheath from its stored condition, the sheath being shaped to easily cover the illumination assembly.

Removal of the reusable illumination assembly is also done advantageously in which removal of the disposable portions (speculum, sheath assembly) of the system can be easily accomplished following use of the speculum by holding the assembly over a refuse container and maintaining hold of the extending electrical cord of the illumination assembly and pushing the sheath downwardly such that contamination does not cover the illumination assembly while making the disposable portions easily discardable.

These and other objects, features and advantages will become readily apparent from the following Detailed Description which should be read in conjunction with the accompanying drawings.

DETAILED DESCRIPTION

The following description relates to the incorporation of a protective sheath for use with a specific disposable vaginal speculum assembly. It will be readily apparent to one of sufficient skill in the field, however, that the inventive concepts described herein are applicable to various speculums of differing designs and should not be regarded as being limited to that described herein.

Figure 1:
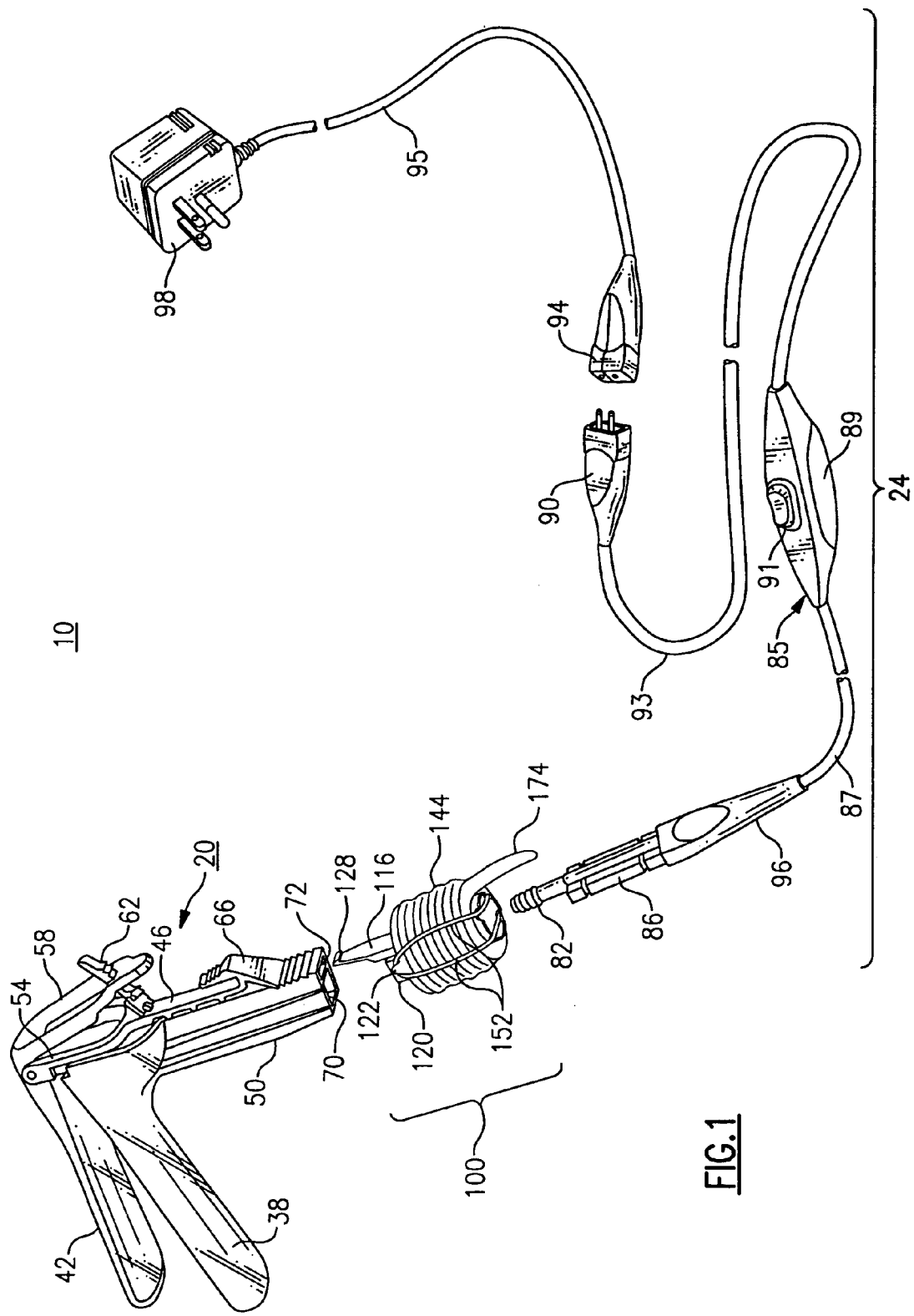
FIG. 1 is a front perspective view of a disposable vaginal speculum assembly including a protective sheath made in accordance with a preferred embodiment of the present invention.

Referring to FIG. 1, there is shown a disposable vaginal speculum system 10 in accordance with the present invention. The herein described speculum system 10 includes a disposable vaginal speculum 20, an illumination assembly 24, and a protective sheath assembly 100.

Figure 2:
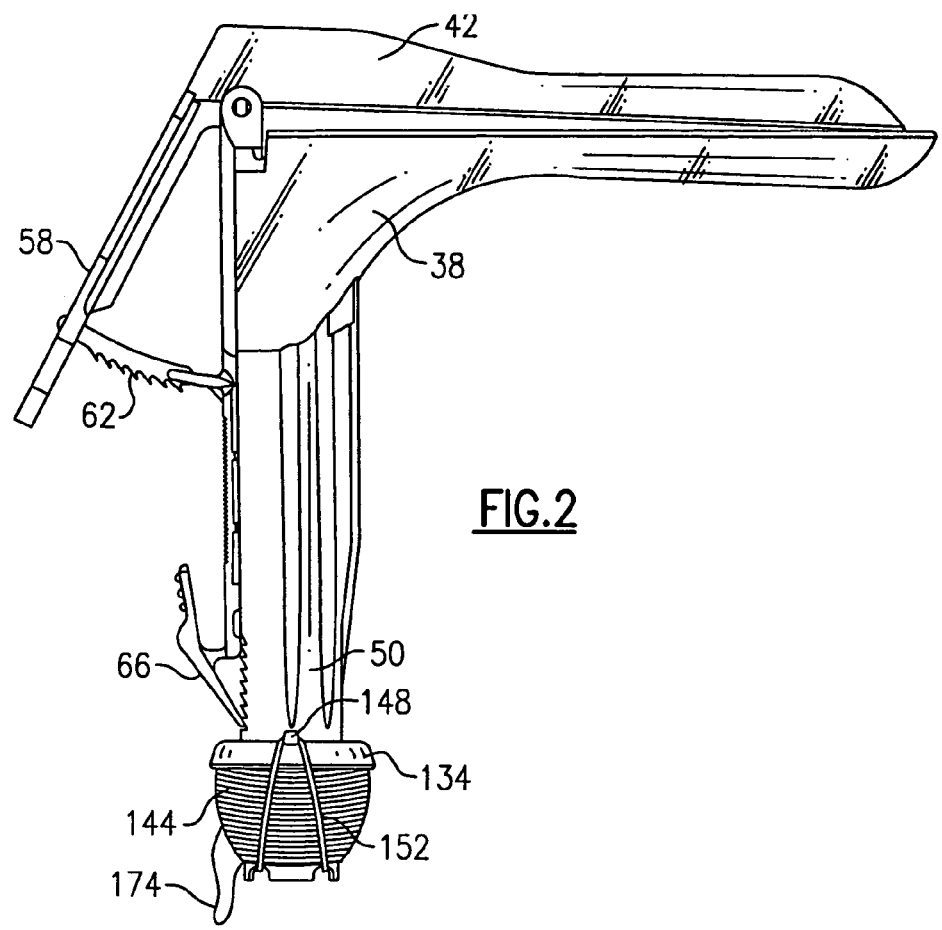
FIG. 2 is a side elevational view of the vaginal speculum depicting the interconnection of the protective sheath of FIG. 1.
Figure 2A:
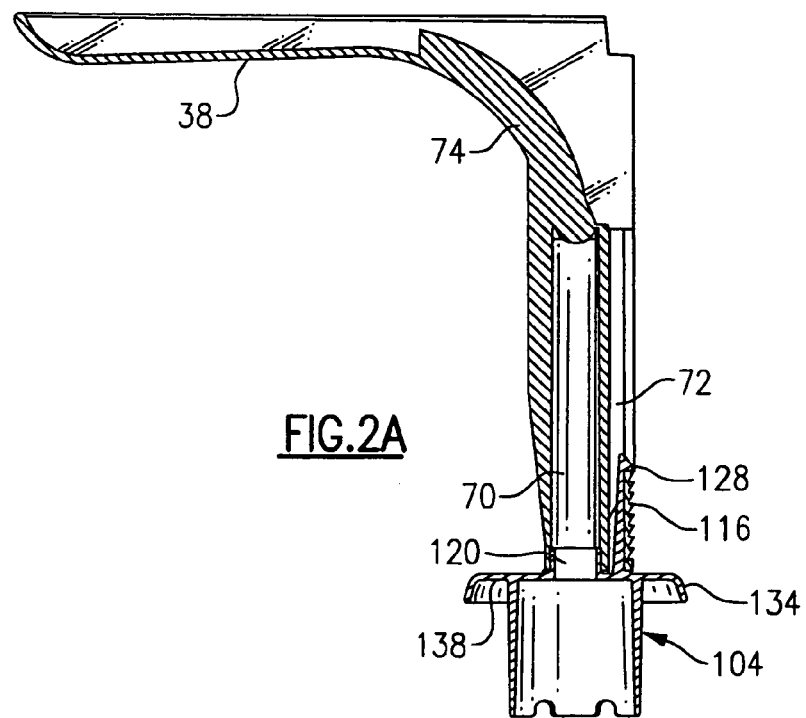
FIG. 2A is a side elevational view, in section of a fixed blade member of the vaginal speculum of FIG. 1 and an attached sheath supporting member.
Figure 3:
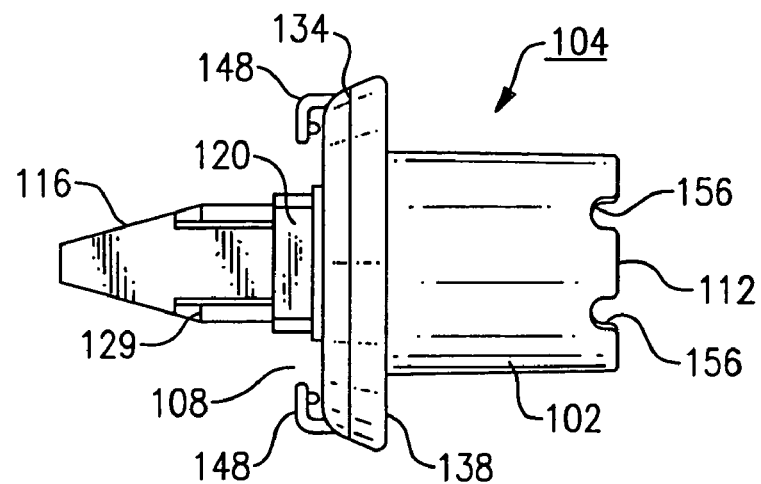
FIG. 3 is a side view of the sheath supporting member of FIGS. 1–2A.

More particularly and as shown in FIGS. 1, 2 and 2A, the disposable vaginal speculum 20 includes three main interconnected components; namely, a fixed blade member 38, a movable blade member 42 and a slide member 46. Each of the fixed blade member 38 and the movable blade member 42 are preferably made from a clear, inflexible plastic material, such as acrylic or polystyrene, in which the fixed blade member 38 includes a trough shaped blade and a hollow leg 50 that forms a handle for the user of the speculum 20. The slide member 46 is preferably made from a resilient plastic material, such as polypropylene, includes a forked upper end 54 that receives the movable blade member 42 which is pivotally attached thereto, including a lever portion 58 that is adjustably attached via a ratchet mechanism 62 provided on the top of the slide member 46. In addition, the slide member 46 includes a lower tongue 66 having ratchet teeth that engage with corresponding teeth provided on the rear side of the hollow leg 50 of the fixed blade member 38 of the disposable vaginal speculum 20 to provide further adjustment therebetween.

The hollow leg 50 of the fixed blade member 38 of the disposable vaginal speculum 20 includes a pair of parallel slots 70, 72. Slot 70 is sized for receiving a portion of the illuminator assembly 24 as well as aligning the inserted illuminator assembly portion relative to an interior curved light bar 74, shown in FIG. 2A, that receives the light from a miniature incandescent lamp (not shown) contained in the inserted portion of the illuminator assembly 24 and directs it along a longitudinal axis of the fixed blade member 38. Additional details concerning the components and overall operation of the herein described disposable vaginal speculum 20 can be found in U.S. Pat. No. 3,716,047, the entire contents of which are herein incorporated by reference.

Still referring in general to FIG. 1, the illumination assembly 24 includes a miniature light source, such as a miniature incandescent halogen lamp (not shown), that is disposed within a lamp housing 82 that is threaded into the distal end of an enclosure 86. The enclosure 86 is that portion of the illumination assembly 24 that is placed into the slot 70 of the disposable vaginal speculum 20. The enclosure 86 includes a gripping portion/strain relief 96 at a proximal end thereof to permit a user to insert or remove the enclosure of the illumination assembly 24 from the interior of the hollow end 50 of the disposable vaginal speculum 20. A cord 87 extends from the gripping portion/strain relief 96 of the enclosure 86, the cord containing a number of electrical conductors (not shown) connected to electrical contacts provided in the enclosure.

An in-line illumination switch assembly 85 is attached to a proximal end of the cord 87, the in-line switch assembly including a cover housing 89 having an integral switch 91 to permit selective energization of the lamp. The cover housing 89 is tapered, preferably, and includes strain reliefs on opposite sides thereof, interconnecting the enclosure 86 and a power supply, such as a transformer 98, in which a second cord 93 containing electrical conductors extends from the in-line switch assembly to a plug 90 that is fittable with a mating plug 94 that is tethered by a third cord 95 to the transformer 98 in order to selectively supply electrical power to the enclosed halogen lamp.

The lamp housing 82 includes an electrical contact (not shown) at its proximal end that engages corresponding electrical contacts inside the enclosure 86, the housing including an internal O-ring (not shown) that is initially fused with the lamp envelope to form a substantial fluid-tight seal to prevent contaminants from entering the lamp housing 82 and enclosure 86 as described in copending and concurrently filed USSN (to be assigned) (Attorney Docket No. 281_392). The foregoing seal provides an advantage in that the enclosure 86 can now undergo sterilization procedures.

Referring to FIGS. 1, 2A, 3 and 4, the protective sheath assembly 100 includes a sheath supporting member 104 defined by a short hollow cylindrical tubular housing 102 having a distal end 108 and a proximal opening 112. The distal or connecting end 108 of the sheath supporting member 104 includes an outwardly extending pawl 116 adjacent a rectangular shaped insertion portion 120 having a distal opening 122, the insertion portion being sized for engaging the slot 70 formed in the proximal end of the hollow leg 50 of the speculum 20. The rectangular opening 122 is also sized to receive the molded body of the enclosure 86 of the illumination assembly 24, permitting the enclosure to pass therethrough into the slot 70 of the disposable vaginal speculum 20. The extending pawl 116 includes an engagement tooth 128 at its distalmost end and a thickened base portion 129 for positively engaging with the interior of the rear wall of the hollow leg 50 of the speculum 20, the tooth engagement being shown in FIG. 2A.

The distal end 108 of the sheath supporting member 104 further includes an annular receiving portion 134 having a diameter that is larger than that of the tubular housing portion 102, the receiving portion including a concave supporting surface 138.

The exterior or distal facing side of the annular receiving portion 134 includes a plurality of support tabs 148 used as a fastening and release means for a stored protective sheath 144 in conjunction with a plurality of spaced corresponding notches 156 provided at the proximal end of the tubular support portion 102 of the sheath supporting member 104. As detailed below, an elastic band 152 or other restraining means is looped over the support tabs 148 and notches 156 to provide support when placed along protective sheath 144, holding compressing and retaining the sheath in place, Referring to FIGS. 1, 2, 4 and 5, the protective sheath 144 is a highly flexible, thin plastic sleeve-like member having a cylindrical configuration that when deployed is sized so as to cover the illumination assembly 24, including the cords 87, 93 and the in-line switch assembly 85. Preferably, the protective sheath 144 is made from polyethylene, though other suitable materials can be used, transparent or otherwise. It is not required, however, that the protective sheath 144 necessarily be constructed from a biocompatible material. In terms of preassembly, one end of the sheath 144 is fixedly attached by adhesive tape or other means to the sheath supporting member 104 and more particularly at the proximal side of the annular supporting portion 134. In terms of compressing into the stored condition on the sheath supporting member 104, the protective sheath 144 is initially extended and then compressed to be formed into its stored condition such that release of the elastic band 152 from the retaining means of the sheath supporting member 104 will permit the sheath to drop over the illumination assembly 24, including the in-line switch assembly 85, as described in greater detail below. Finally, the opposite end of the protective sheath 144 forms an protruding tail 174 extending from remainder of the compressed sheath, the tail providing a guide for the user during deployment and further including a tapered portion to assist in guiding the sheath over the in-line switch assembly.

Referring now to FIGS. 5–9, the operation of the herein described invention is summarized in use.

Figure 4:
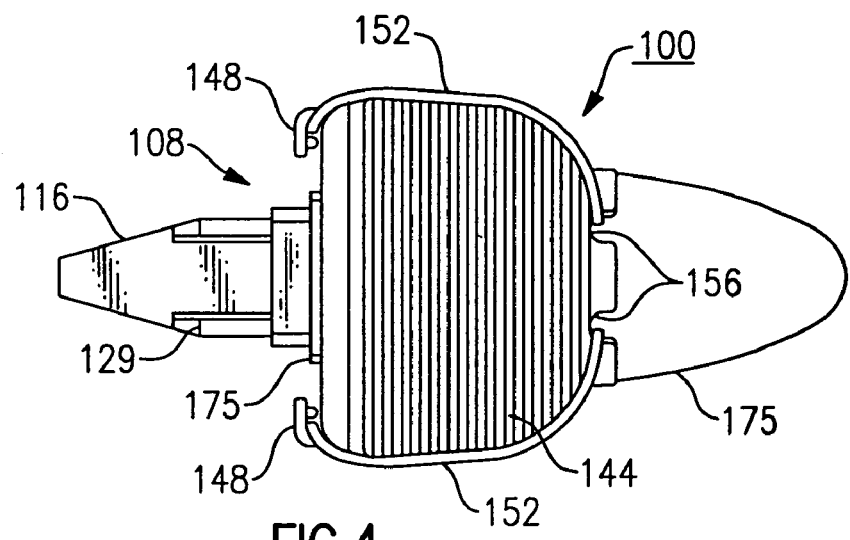
FIG. 4 is the side view of the sheath supporting member of FIG. 3 with a sheath attached thereto.
Figure 5:
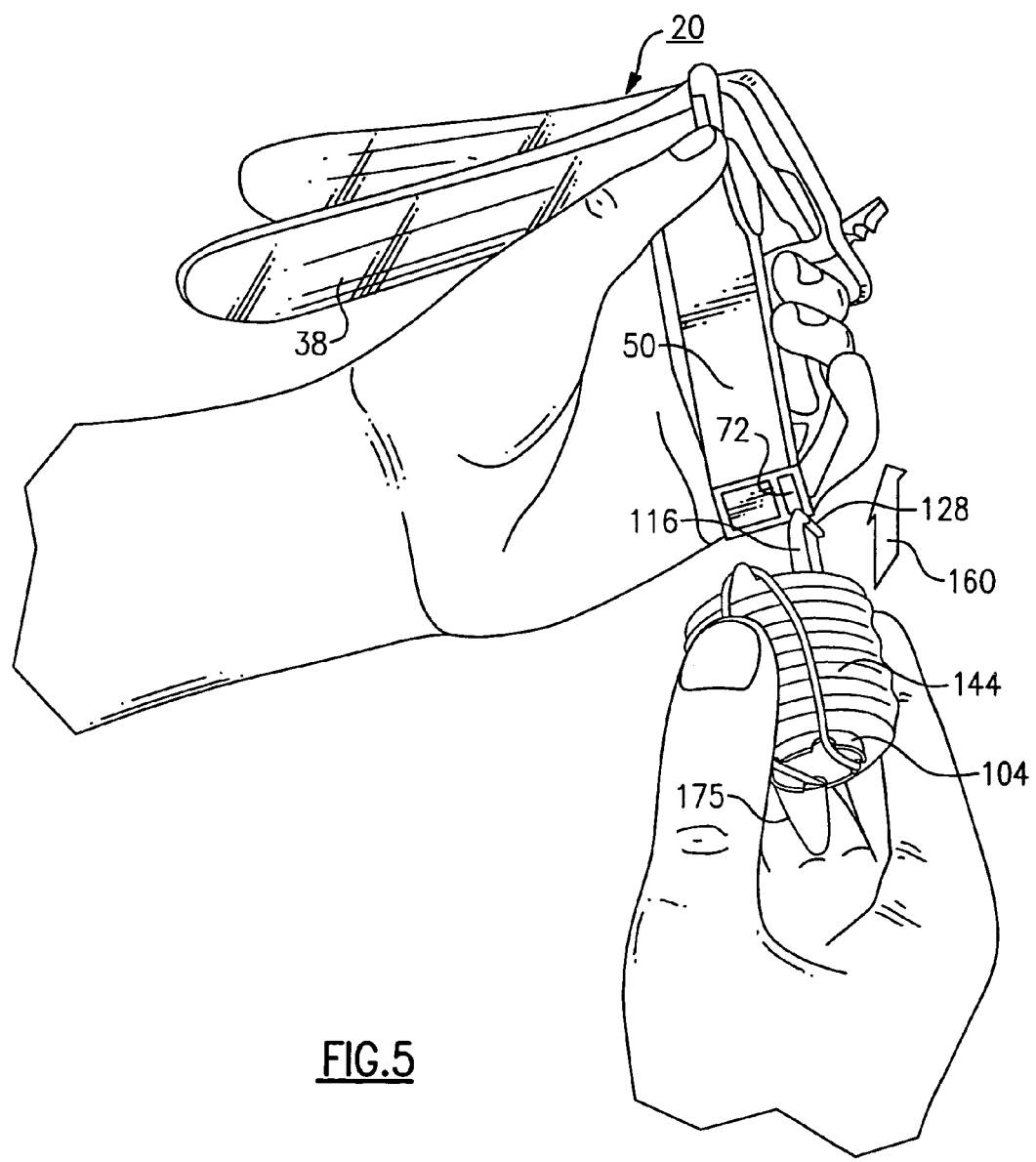
FIGS. 5–9 are sequential in-use depictions of the protective sheath relative to the disposable vaginal speculum assembly.

First and referring to FIGS. 2A and 5, the sheath supporting member 104 is attached to the proximal end of the fixed blade member 38 of the disposable vaginal speculum 20 with the protective sheath 144 already compressed in the stored condition as described above. The sheath supporting member can be provided integrally with the speculum as part of an assembly or can be separately purchased and installed by the user. The sheath supporting member 104 is attached to the disposable vaginal speculum 20 by properly aligning the extending pawl 116 at the distal end 108, FIG. 4, thereof with slot 72 of the hollow leg 50 of the speculum 20 and the insertion portion 120, FIG. 2A, with slot 70 and then pushing the supporting member into place according to arrow 160, until the engagement tooth 128 positively engages with the interior of the rear wall of the hollow leg 50.

Referring briefly to FIG. 4, an O-ring 175 is also preferably installed onto the exterior of the insertion portion 120. This O-ring 175 functions to take up slack for mold cavity variability in the manufacture of the sheath supporting member 104 and further provides additional protection from fluid ingress.

Figure 6:
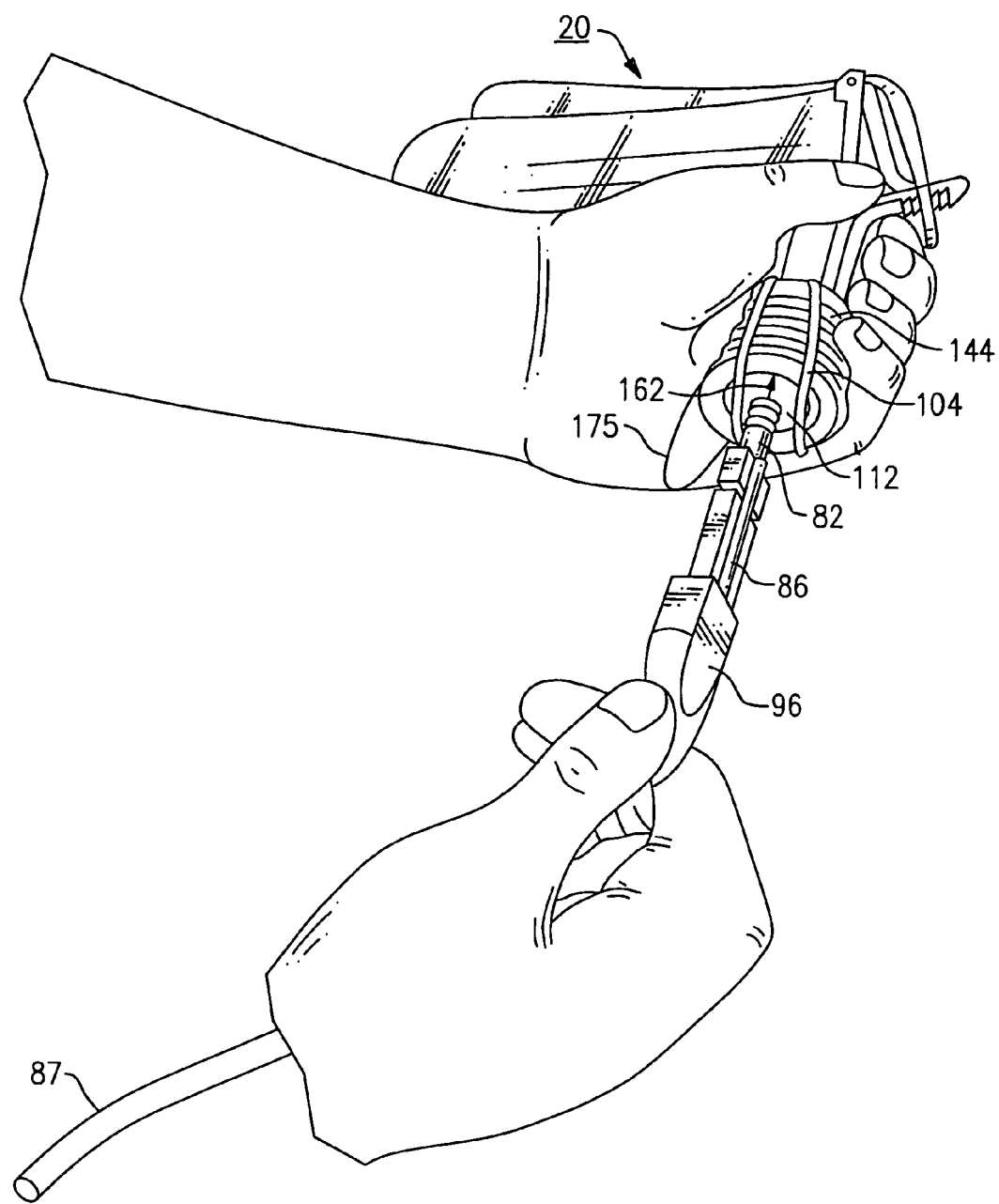

Next and referring to FIG. 6, the enclosure 86 of the illumination assembly 24 is then inserted as held by enclosure 86 through the proximal opening 112 and the rectangular opening 122 defined in the distal insertion portion 120, FIG. 2A, of the assembled sheath supporting member 104 and into the slot 70, FIG. 2A, of the hollow leg 50 of the disposable vaginal speculum 20, sized to retain the enclosure 86 in a manner that is conventionally known, as indicated by arrow 162.

Figure 7:
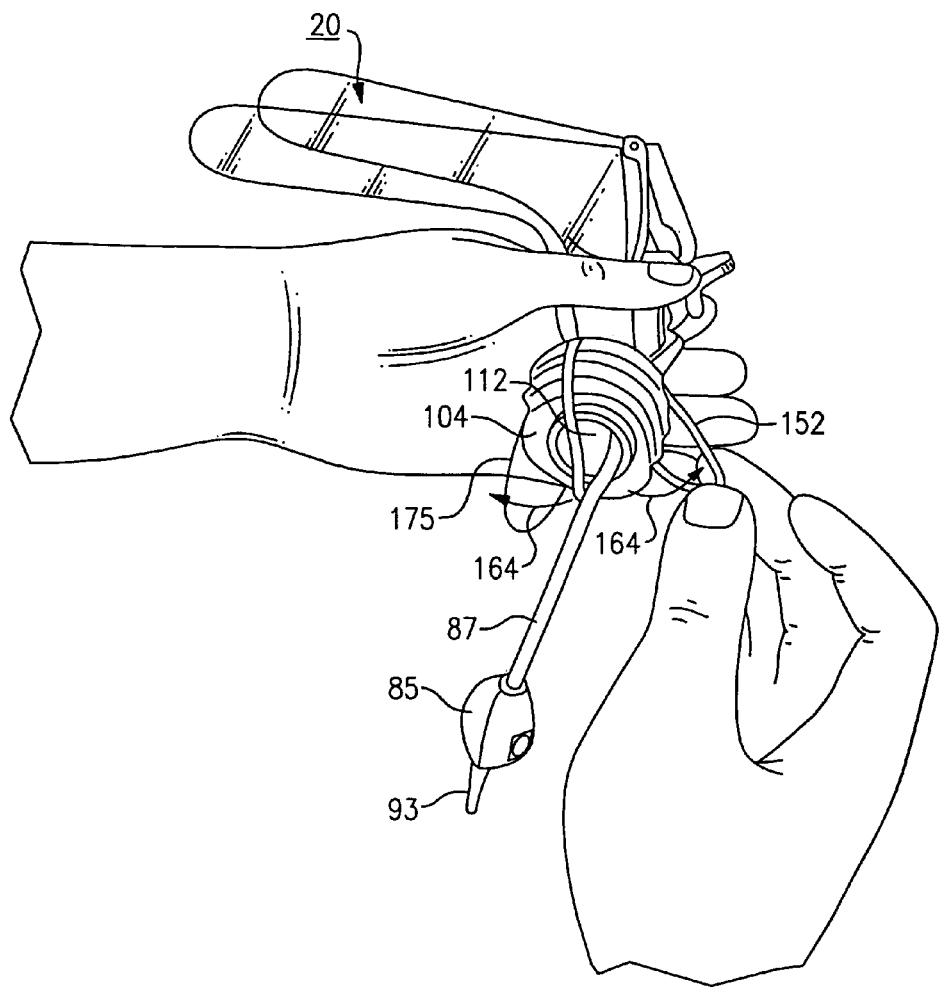
Figure 8:
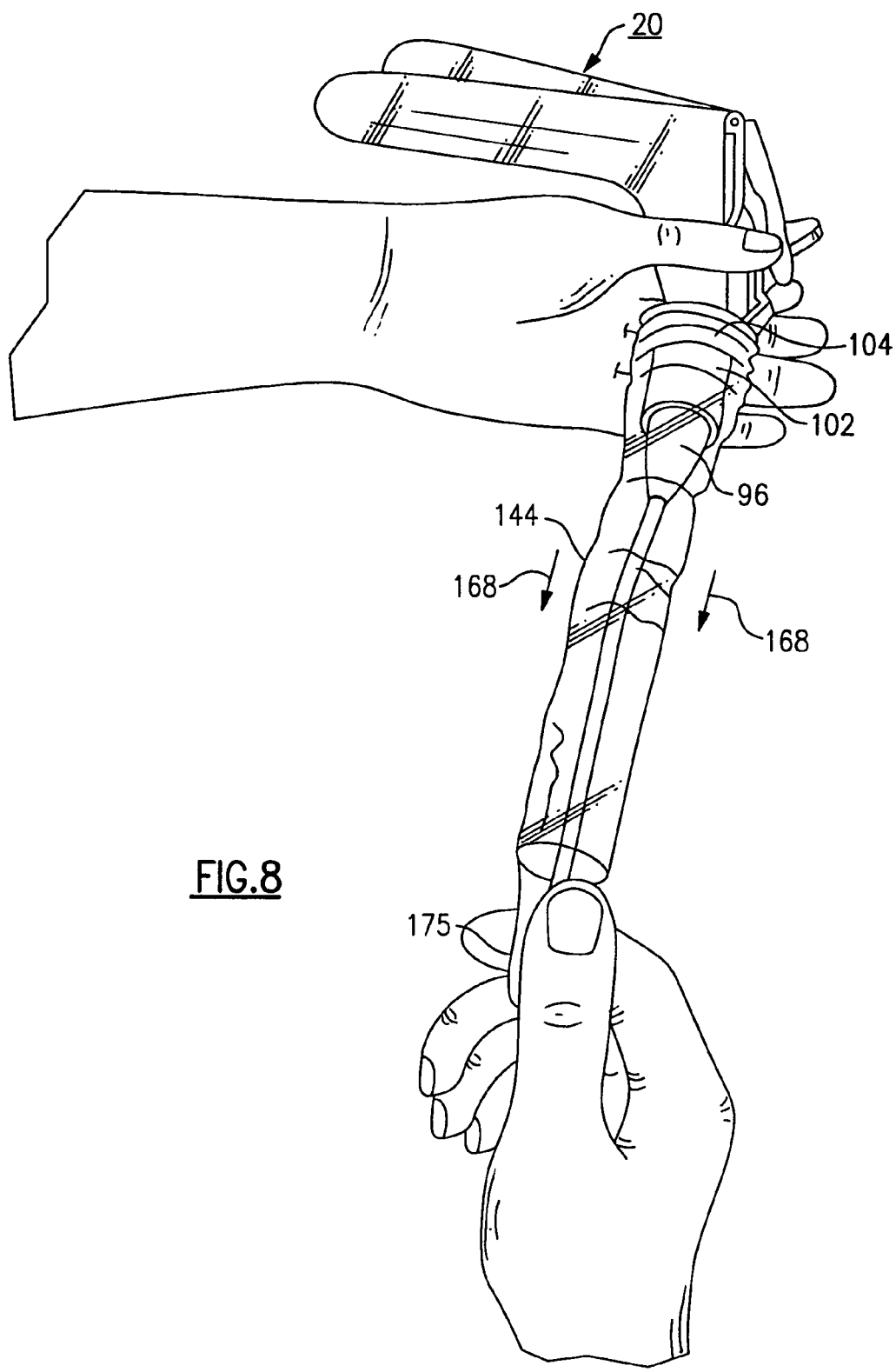

Next and referring to FIGS. 7 and 8, the protective sheath 144 is deployed by detaching the elastic band 152 from the supporting tabs 148 and notches 156, arrows 164, in order to release the sheath from its stored compressed condition on the sheath supporting member 104. Following the release of the elastic band, the tail 174, FIG. 1, of the deployed protective sheath 144 is then pulled downwardly so as to cover the depending cord and the in-line switch portions of the illumination assembly 24, as shown by arrows 168 in FIG. 8.

The protective sheath 144 is shaped so as to permit the sheath to be easily pulled over the illumination assembly, including the in-line switch assembly 85, as shown by arrows 168. The physician can then use the use the system 10 to conduct an examination of the patient in the conventional manner. The illumination assembly 24 is energized by activating switch 91 of the in-line switch assembly 85, which can easily be activated through the protective sheath 144 while the sheath covers this portion of the assembly.

Figure 9:
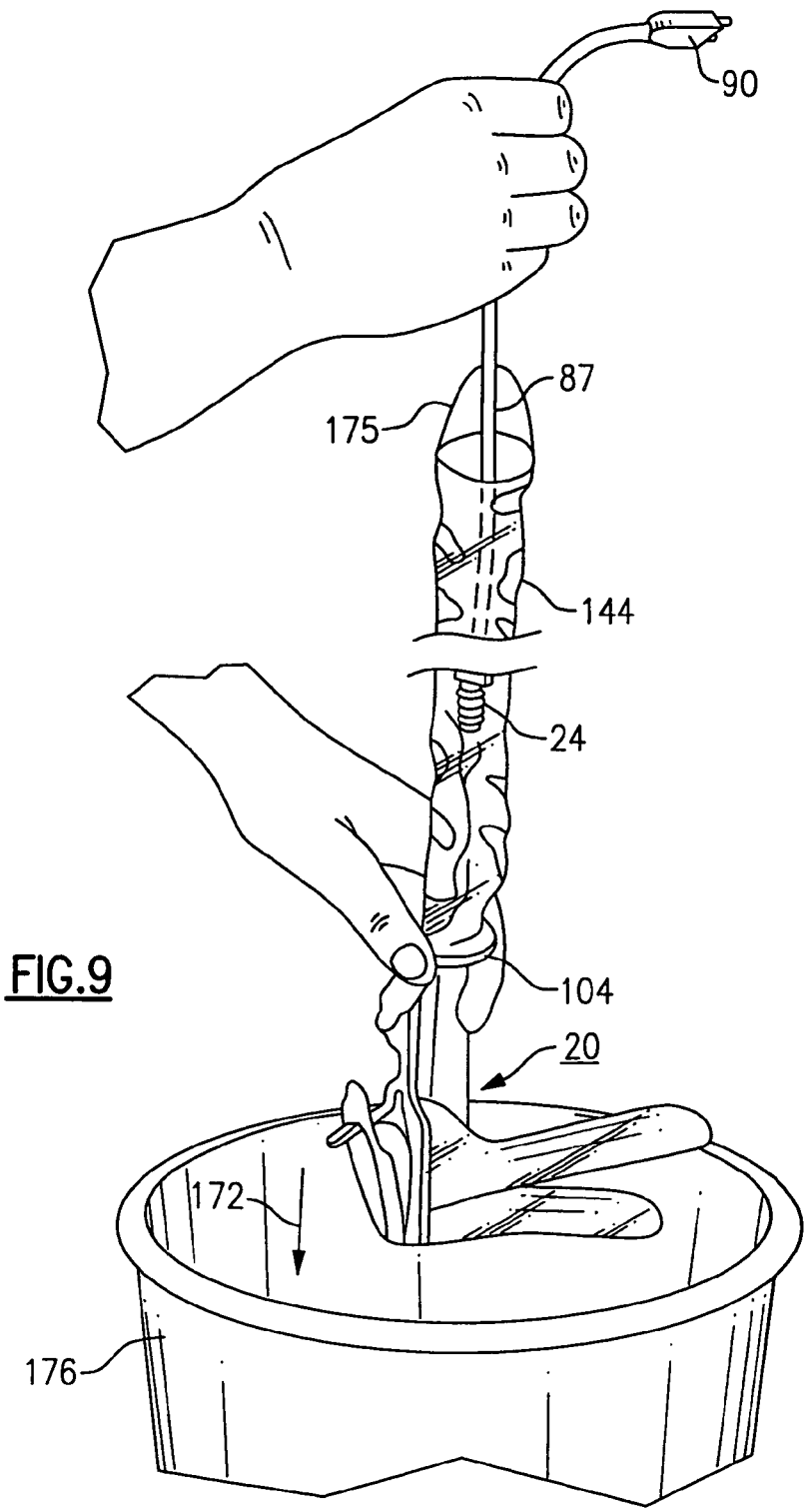
Figure 3:
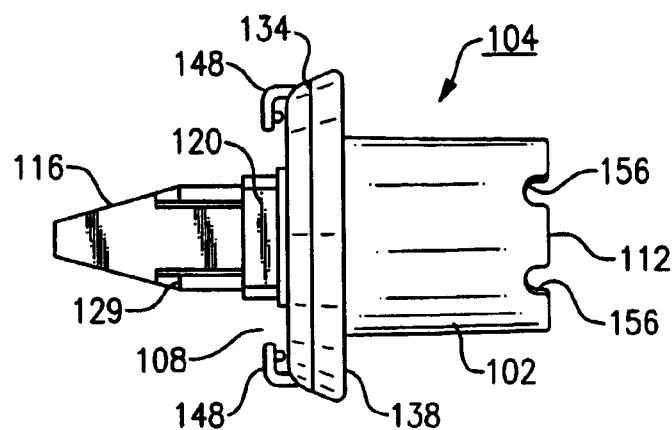
Figure 4:
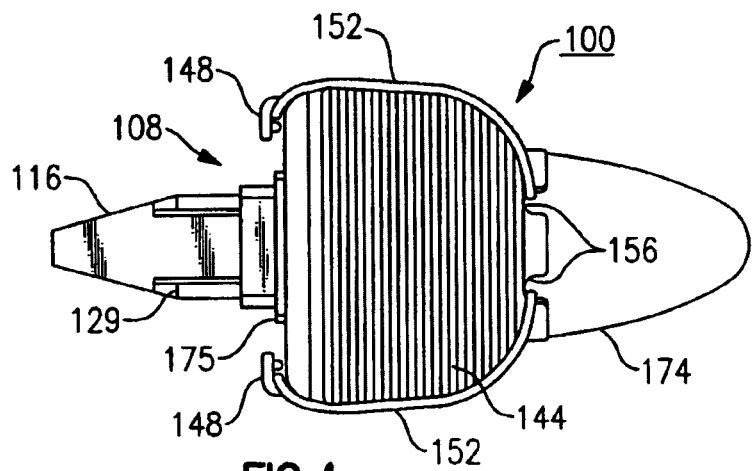
Figure 5:
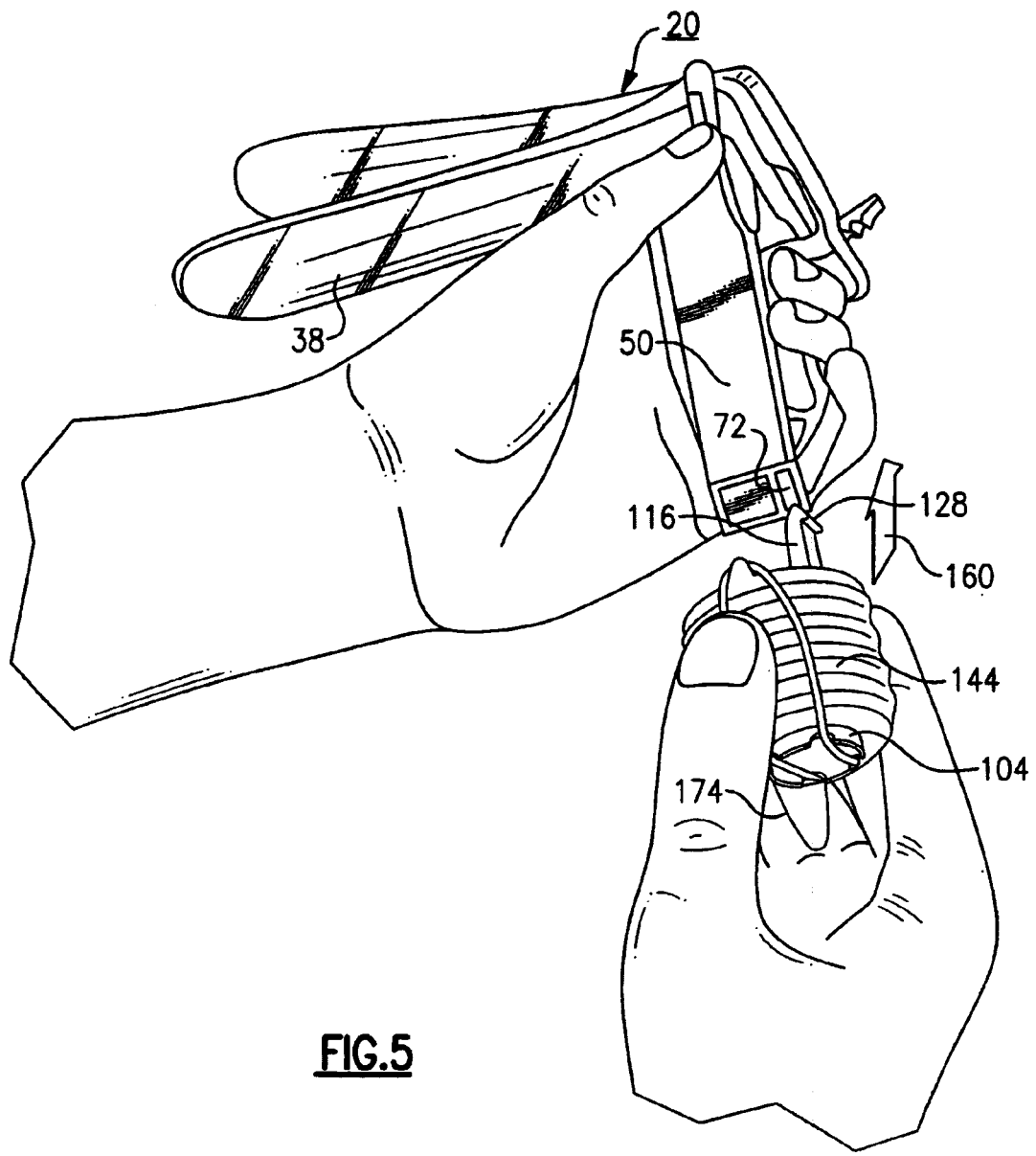
Figure 6:
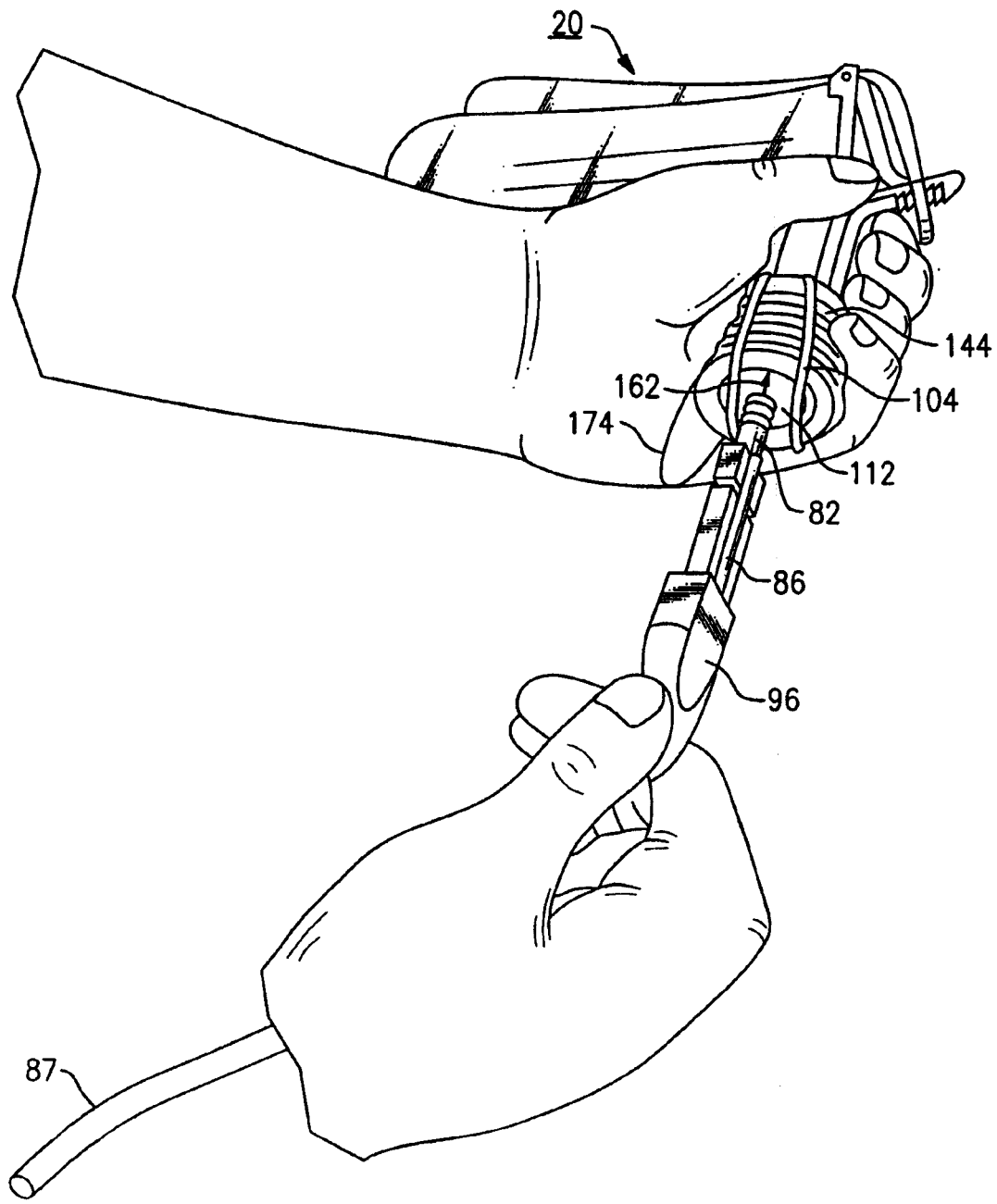
Figure 7:
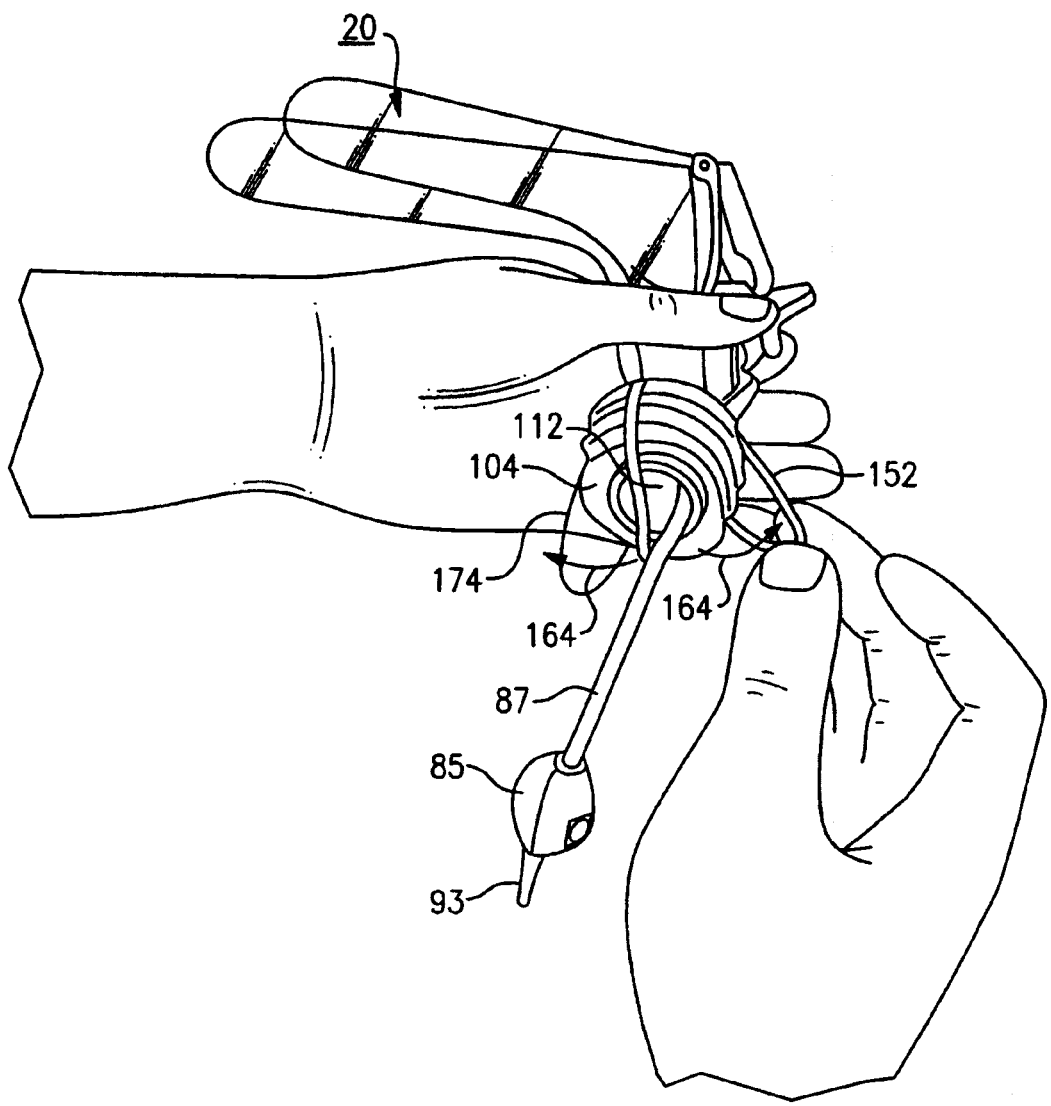
Figure 8:
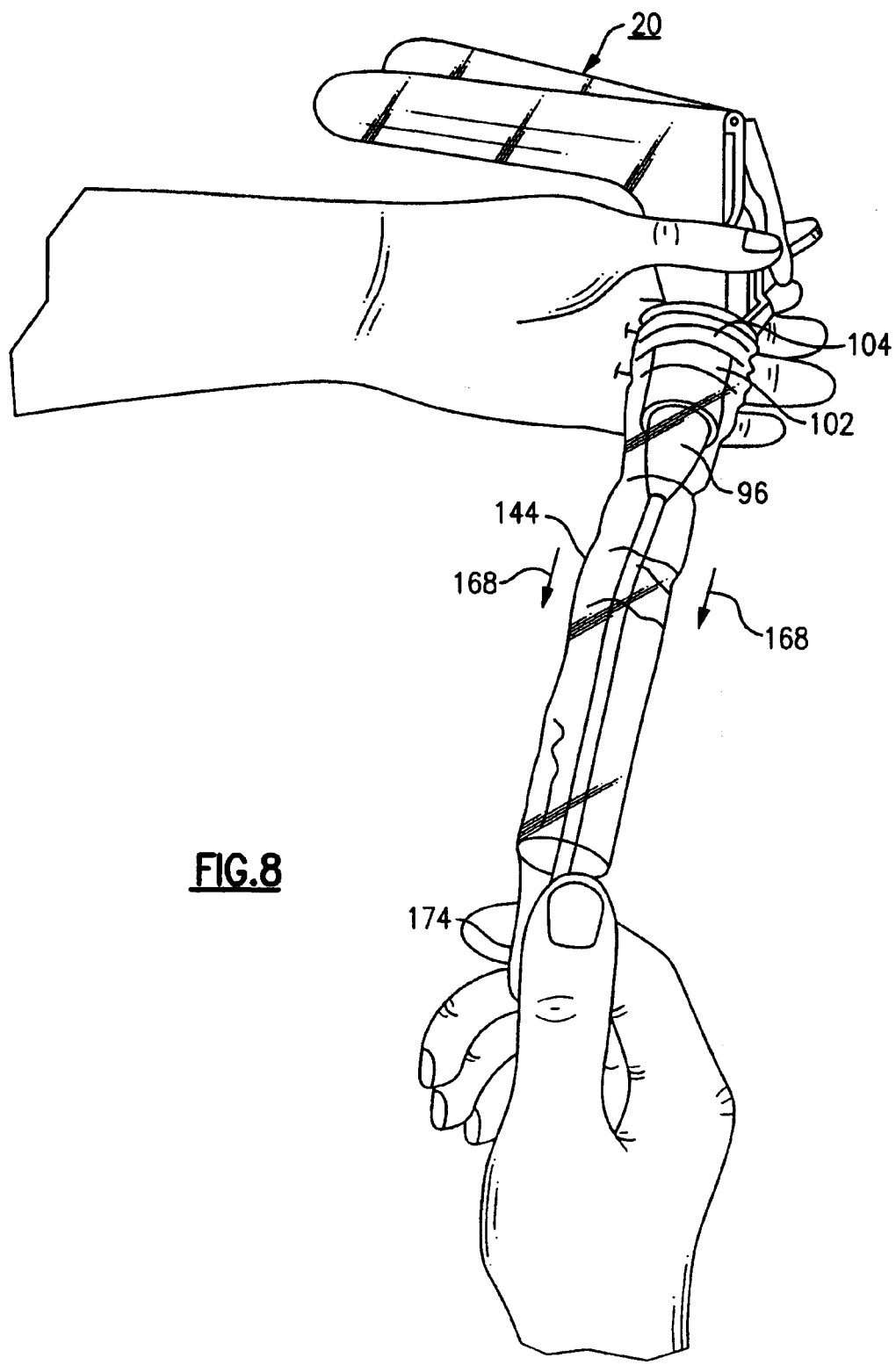
Figure 9:
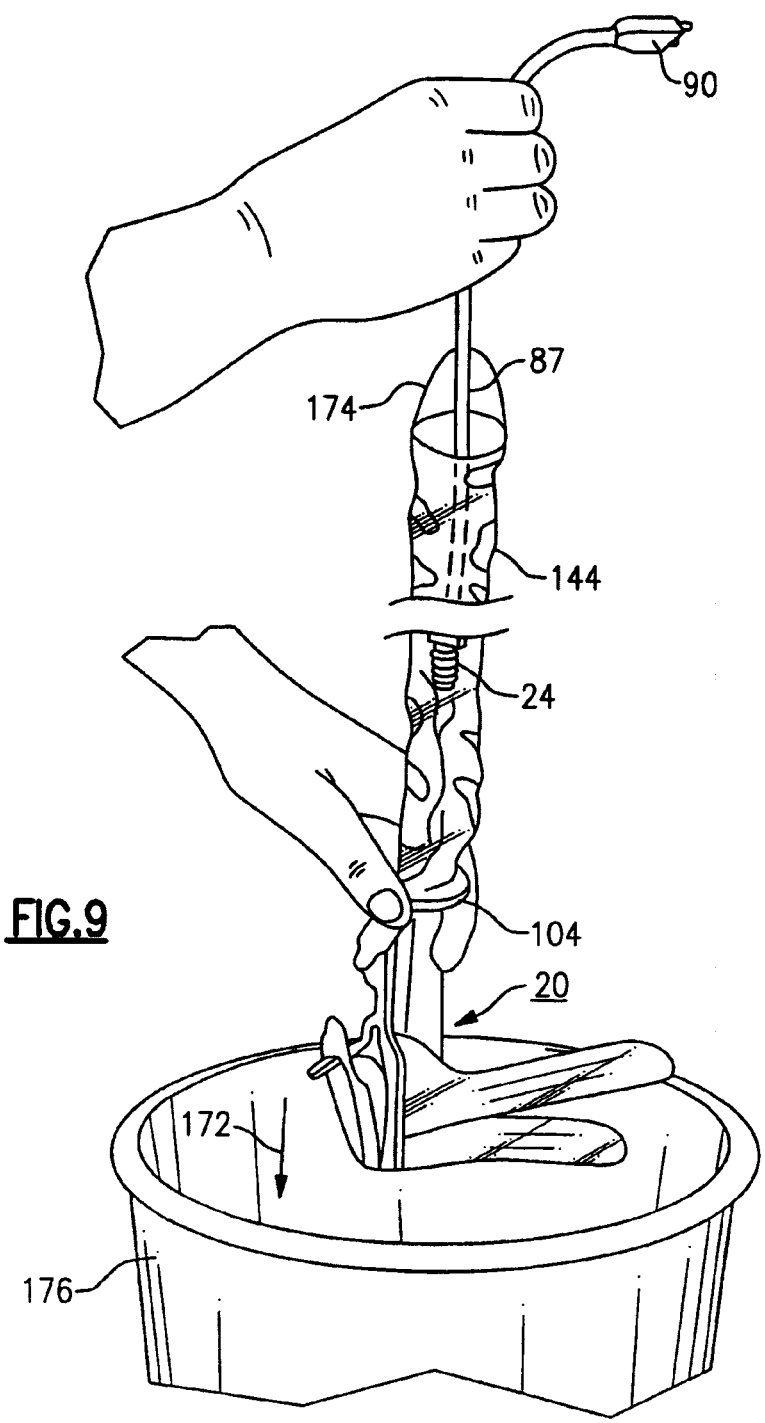

Following examination and referring to FIG. 9, the illumination assembly 24 is turned off and the transformer 98 is disconnected from the remainder of the stem 10. The remainder of the assembly can then be placed over a refuse container 176, holding the extending proximal end of the cord 93 of the illumination assembly 24 and pulling downwardly, the illumination assembly can be released from the disposable speculum 20 such that the speculum and the attached protective sheath 144 can be easily discarded, shown by arrow 172.

PARTS LIST FOR FIGS. 1–9

10 disposable vaginal speculum system
20 disposable vaginal speculum
24 illumination assembly
38 fixed blade member
42 movable blade member
46 slide member
50 hollow leg
54 forked upper end
58 lever portion
62 ratchet mechanism
66 lower tongue
70 slot
72 slot
74 interior curved light bar
82 lamp housing
85 in-line illumination switch assembly
86 enclosure
87 cord
89 cover housing
90 plug
91 switch
93 cord
94 plug
95 cord
96 gripping portion/strain relief
98 transformer
100 protective sheath assembly
102 tubular supporting portion
104 sheath supporting member
108 open end-distal 112 open end-proximal
116 pawl
120 opening
128 engagement tooth
129 base portion
134 annular receiving portion
138 supporting surface
144 protective sheath
148 support tabs
152 elastic band
166 notches
160 arrow
162 arrow
178 arrow
172 arrow
174 tail
175 O-ring
176 refuse container Though the present invention has been described with reference to the preferred mode as illustrated in the drawings, it will be understood by one skilled in the art that various changes in detail may be effected therein without departing from the spirit and scope of the invention as defined by the claims. For example, it should be readily apparent that other designs can be implemented for supporting the protective sheath prior to release. For example and in lieu of the support tabs, a strap, a single tab (not shown) or a cover could be used. Alternatively, adhesives, tape or other bonding means could also be substituted.

We claim:

1. A protective sheath assembly for use with a disposable vaginal speculum, said protective sheath assembly comprising:
a support member adapted to be attachable to the handle of said speculum and including means for retaining a protective sheath in a stored position prior to use of said speculum, said support member including at least one engagement feature for engaging said speculum handle and a through opening to permit the inclusion of a portion of an illumination assembly therethrough.

2. An assembly as recited in claim 1, including release means for releasing said protective sheath from said stored position and deploying same so as to cover at least a portion of an illumination assembly that is attached to said speculum.

3. An assembly as recited in claim 1, wherein said support member is defined by a tubular support portion onto which said protective sheath is stored, said support member further including an annular receiving portion for receiving one end of said sheath.

4. An assembly as recited in claim 3, wherein the tubular support portion has a diameter which is less than the diameter of said annular receiving portion, said annular receiving portion further including a concave receiving surface for receiving the end of said sheath.

5. An assembly as recited in claim 3, wherein one end of said protective sheath is fixedly attached to said tubular support portion.

6. An assembly as recited in claim 5, wherein said fixed end is taped to said tubular support portion.

7. An assembly as recited in claim 1, wherein said retaining means includes at least one elastic member wrapped along said protective sheath, said support member including support features for retaining said elastic member in compressive contact with said stored sheath.

8. An assembly as recited in claim 1, wherein the at least one engagement feature of said support member includes a protruding pawl adapted for engaging a first slot formed in the handle of a disposable speculum.

9. An assembly as recited in claim 8, wherein said support member includes an insertion portion adapted for engaging a second slot formed in the handle of a disposable speculum.

10. An assembly as recited in claim 9, wherein said insertion portion includes said through opening sized to accommodate a portion of an illumination assembly.

11. An assembly as recited in claim 1, wherein said sheath includes a tail portion that assists in the deployment of said sheath from said stored position.

12. An assembly as recited in claim 11, wherein said tail portion is tapered.

13. A vaginal speculum assembly comprising:
a disposable speculum having a handle;
an illumination assembly including a light source retained within a housing that is releasably attached to said speculum, wherein at least a portion of said illumination assembly extends from said housing;
a protective sheath;
a support member attachable to the handle of said speculum onto which said protective sheath is mounted in a stored condition, said support member including at least one engagement feature to permit attachment to said handle and a through opening sized for permitting at least a portion of said illumination assembly to pass therethrough into said handle;
wherein said sheath is deployable, releasing said sheath from its stored condition on said support member so as to cover said illumination assembly including a portion of said extending portion during an examination process.

14. The assembly as recited in claim 13, wherein said support member includes retaining means for retaining the protective sheath in said stored condition until the user has mounted the illumination assembly to the disposable speculum prior to the examination process.

15. The assembly as recited in claim 14, wherein said retaining means includes at least one elastic member which is held in contact against the stored sheath, the at least one elastic member being held by at least two supporting features appropriately located on the support member.

16. The assembly as recited in claim 13, wherein said support member retains the protective sheath as a compressed cylinder overlaying a spool-like portion of the member in the stored condition, said support member being hollow and including an opening through which a portion of the illumination assembly passes.

17. The assembly as recited in claim 13, wherein the sheath includes a tail portion that assists in the deployment of the sheath from its stored position.

18. The assembly as recited in claim 17, wherein said tail portion is tapered.

19. The assembly as recited in claim 13, wherein through opening of said support member is sized for permitting said housing retaining said light source to pass therethrough.

20. The assembly as recited in claim 19, wherein said illumination assembly further includes a cord tethered to said lamp housing and an inline switch assembly, said sheath being shaped for covering said in-line switch assembly and at least a portion of said cord.

21. The assembly as recited in claim 13, wherein one end of said protective sheath is fixedly retained by said sheath support member.

22. The assembly as recited in claim 13, wherein the at least one engagement feature of said support member includes an extending pawl sized for engaging a first slot formed in said handle of said disposable speculum, said pawl including an engagement tooth.

23. The assembly as recited in claim 22, wherein support member includes an insertion portion sized for fitting within a second slot formed in said handle of said disposable speculum.

24. The assembly as recited in claim 23, wherein said at least a portion of said illumination assembly is fitted into said handle of said speculum through said opening formed in said insertion portion.

25. The assembly as recited in claim 23, including an O-ring fitted to the exterior of said insertion portion to provide a fluid tight seal between said insertion portion and said second slot.

26. The assembly as recited in claim 13, wherein said protective sheath is compressed onto said support member when in said stored condition.

27. The assembly as recited in claim 13, wherein said support member is attachable to a speculum handle by a user of said speculum.

28. The assembly as recited in claim 13, wherein said support member is mounted to said speculum handle in the manufacture thereof.

29. A method for protecting an illumination assembly of a disposable vaginal speculum from contamination during use thereof, said speculum including a hollow handle, said method comprising the steps of:
  attaching a protective sheath assembly to said disposable speculum prior to use thereof, said sheath assembly including a support member that is mounted to the handle of said speculum and a protective sheath that is disposed on said support member in a stored condition, said support member being attached to said handle using at least one engagement feature provided on said support member;
  attaching the illumination assembly to said disposable speculum through an opening extending through said support member; and;
  deploying said protective sheath from said stored condition prior to use of said speculum so as to cover an extending portion of said illumination assembly.

30. A method as recited in claim 29, including the step of compressing said protective sheath onto said support member prior to said protective sheath assembly attaching step so as to place said sheath in a stored condition.

31. A method as recited in claim 29, wherein said attaching step includes the step of wrapping at least one elastic member along the exterior of said compressed protective sheath.

32. A method as recited in claim 31, wherein said deploying step includes the step of releasing said at least one elastic member from said protective sheath.

33. A method as recited in claim 29, wherein said protective sheath assembly attaching step includes the further step of engaging a protruding pawl of said support member into a first slot of said handle of said speculum.

34. A method as recited in claim 33, wherein said illumination assembly attaching step includes the further step of inserting a lamp housing portion of said illumination assembly through said opening in said support member extending into a second slot of said handle of said speculum.

35. A method as recited in claim 33, including the step of attaching an insertion portion of said support member to a second slot of said hollow handle, said insertion portion including said through opening for receiving said illumination assembly.

36. A method as recited in claim 35, including the step of providing a fluid-tight seal between said insertion portion and said second slot.

37. The method of claim 29, further including the additional step of placing the speculum and attached illumination assembly over a refuse container and while still holding the extending cord of the illumination assembly, pushing downwardly on the speculum, thereby easily discarding the remainder of the assembly following use thereof.

* * * * *

UNITED STATES PATENT AND TRADEMARK OFFICE
CERTIFICATE OF CORRECTION

| | | |
|---|---|---|
| PATENT NO. | : 7,081,090 B2 | |
| APPLICATION NO. | : 10/393848 | |
| DATED | : July 25, 2006 | |
| INVENTOR(S) | : James G. Strong et al. | |

It is certified that error appears in the above-identified patent and that said Letters Patent is hereby corrected as shown below:

Delete Drawing Sheets 3-8 and substitute therefor Drawing Sheets 3-8 (attached)

Column 6 line 27 change "stem" to --system--

Column 7 under Parts List, change reference numeral "178" to reference numeral --168--

Signed and Sealed this

Fourteenth Day of November, 2006

JON W. DUDAS
*Director of the United States Patent and Trademark Office*